Figure 1:
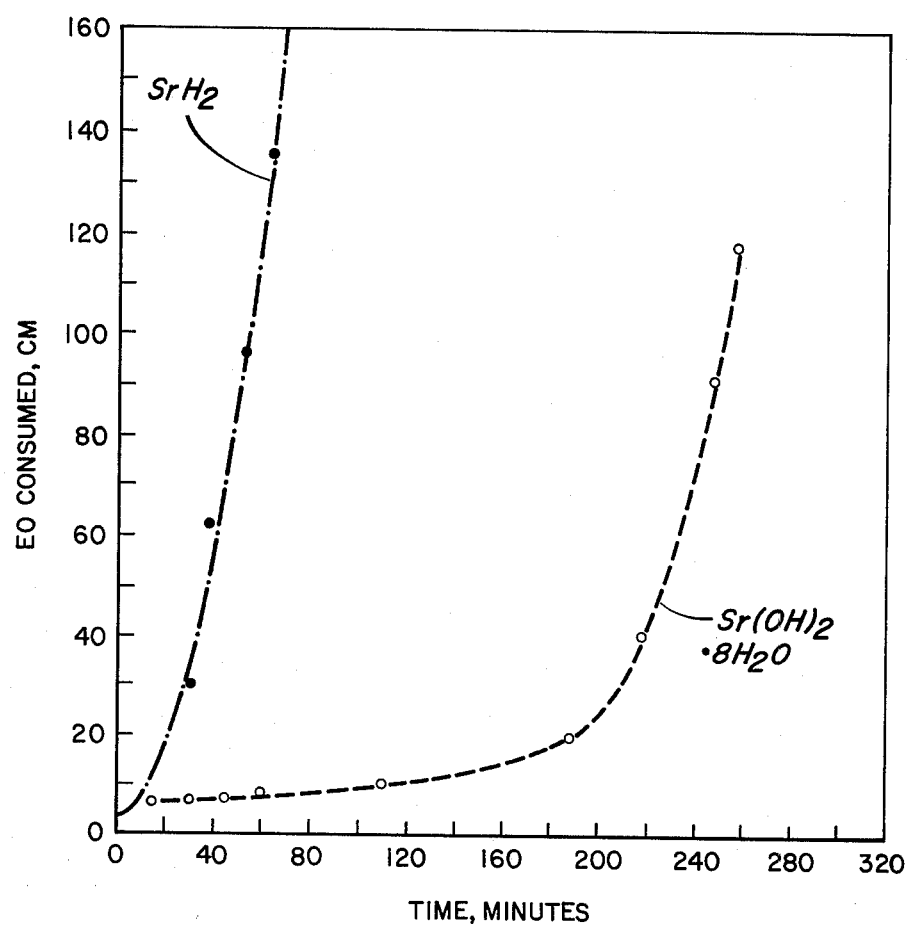

United States Patent [19]

Yang et al.

[11] 4,306,093
[45] * Dec. 15, 1981

[54] STRONTIUM CATALYZED ALKOXYLATIONS

[75] Inventors: Kang Yang; Gerald L. Nield; Paul H. Washecheck, all of Ponca City, Okla.

[73] Assignee: Conoco Inc., Ponca City, Okla.

[*] Notice: The portion of the term of this patent subsequent to Sep. 16, 1997, has been disclaimed.

[21] Appl. No.: 114,868

[22] Filed: Jan. 24, 1980

[51] Int. Cl.³ .............................................. C07C 41/03
[52] U.S. Cl. ................................................... 568/618
[58] Field of Search ..................................... 568/618

[56] References Cited

U.S. PATENT DOCUMENTS

| | | | |
|---|---|---|---|
| 2,807,651 | 9/1957 | Britton et al. | 568/618 |
| 3,328,306 | 6/1967 | Ellis | 568/622 |
| 3,969,134 | 7/1976 | Batka et al. | 568/618 |
| 3,972,948 | 8/1976 | Laemmle et al. | 568/618 |
| 4,223,164 | 9/1980 | Yang et al. | 568/618 |

Primary Examiner—Joseph E. Evans
Attorney, Agent, or Firm—Cortlan R. Schupbach, Jr.

[57] ABSTRACT

Strontium-containing materials catalyze the alkoxylation of alcohols. Strontium produced alkoxylates have sharper alkoxylate distributions, lower free alcohols, lower pour points, and better detergency than alkoxylates obtained from alkali base catalysis.

15 Claims, 1 Drawing Figure

STRONTIUM CATALYZED ALKOXYLATIONS

This invention relates to the production of alkoxylated alcohols by reacting said alcohols with alkylene oxides. More particularly, this invention relates to the production of said alkoxylated alcohols by reacting said alcohols in the presence of strontium-containing compounds as catalysts.

The general reaction of alcohols and materials such as ethylene oxide to form alkoxylated alcohols (ethylene oxide adducts) has long been known and practiced on a commercial scale. For example, ethylene oxide adducts have been used as detergents and cleaning agents, domestic and industrial laundry detergents, detergent builders, polishers, sanitizers and dry-cleaning materials. Other users include the pulp and paper industry and the fiber industry. These materials are especially adapted to these uses since they have functional properties such as wetting power, foaming, emulsifying and dispersing abilities as well as solubilization and detergent abilities.

Much literature is available in the general area of ethoxylation of alcohols. Many references are also available relating to the catalytic ability of various materials and the mechanism and kinetics of these reactions. For example, French Pat. No. 1,365,945 teaches the use of compounds containing an active hydrogen atom reacted with ethylene oxide in the presence of an alkali metal base.

Acidic catalysts in general are also known. However, the ethoxylation of alcohols invariably produces a distribution of various adducts. For example in surfactant applications, an adduct of too few ethylene molecules is not effective because of poor solubility. In contrast, an adduct with too many ethylene oxide molecules is likewise undesirable because surface tension reduction per unit mass decreases drastically with increase in the molecular weight. Thus it has long been essential to produce and use ethoxylates with as sharp a distribution in the desired mole adduct range (5 to 10 usually) as possible. Acid catalyzed reactions as those described above, produce such alkoxylates but these catalysts produce some harmful side products such as dioxane which must be separated and removed prior to use.

Russian Pat. No. 523,074 teaches that alkali metal and various carbonates can be used to catalyze these reactions. The side product formation in the base-catalyzed reactions is very low, but in base-catalyzed reactions the adduct distribution is undesirably broad. The result is that a large proportion of the product obtained is not useful or is less desirable because of distribution.

Representative of but not exhaustive of the art in this area is U.S. Pat. No. 3,328,467 which describes the use of zeolites and modified zeolites as catalysts in ethoxylation reactions. French Pat. No. 1,557,407 uses triethyl oxonium fluoroborate to catalyze such reactions. Indeed, the art abounds with references to alkali metal hydroxides such as sodium and potassium hydroxides, tertiary amines and sodium metal. German Offenlegungsschrift No. 2,639,564 teaches polyalkylation of active hydrogen compounds in the presence of a sodium fluoroborate or perchlorates of metal such as magnesium, calcium, manganese, or zinc. U.S. Pat. No. 3,969,417 uses tertiary oxonium salts as a catalyst.

U.S. Pat. No. 3,830,850 describes adding sodium, potassium, lithium, rubidium, cesium, calcium, barium, or strontium to condense phenols with formaldehyde, then adding ethylene oxide to the condensation product in an ethoxylation reaction. However, all these materials have the disadvantages described and set forth above.

A catalyst which provides low by-product levels typical of base catalysts, yet provides the narrow distribution of the preferred mole adducts obtained from acid catalysts would be of great benefit. Such a catalyst would promote the narrowing of the product distribution curve and would contribute significantly to the intrinsic value of the alkoxylate produced. Such a catalyst is described in U.S. Pat. No. 4,239,917. However, this catalyst has an induction period ranging up to about 20 minutes at 178° C. and produces from 1 to 2% polyethylene glycol in the product. This catalyst is barium-containing and while the barium is generally accepted as safe, is normally used only under close medical supervision and should be avoided in continuous contact. In addition, U.S. Pat. No. 4,223,164 shows ethoxylation with strontium bases together with phenol or alkylphenol co-catalysts. However, it would likewise be of great benefit to avoid use of co-catalysts in order to carry out a reaction.

It is therefore an object of the present invention to provide a catalyst system which will yield a narrow, high mole adduct distribution from the alkoxylation of alcohols while providing low levels of undesirable by-products and unreacted free alcohol. Other objects will become apparent to those skilled in this art as the description proceeds.

It has now been discovered according to the instant invention that the alkoxylation of all classes of alcohols, preferably alkanols, can be carried out in the presence of strontium containing materials in the absence of a co-catalyst. The reaction product has a narrow distribution of various adducts while yielding a very low level of free alcohols and undesirable by-products. Certain strontium materials do not require an induction period while strontium bases used alone require a more lengthy induction period in order to obtain significant reactions. These benefits are obtained by contacting alkanols with the desired alkylene oxide or mixture of oxides in the presence of a catalyst system comprising at least one material selected from the group consisting of strontium metal, strontium hydride, strontium oxide, strontium hydroxide, or hydrated strontium hydroxide.

The instant invention can be carried out at temperatures of from about 90° C. to about 260° C. However, more normal temperatures are from about 120° C. to about 260° C. However, for most practical purposes, commercial operations will normally be carried out in the temperature range of from about 150° C. to about 250° C. Temperatures in the range of from about 160° C. to about 190° C. are most preferred.

Normally, the alcohols reacted under the process of the instant invention will contain from about 2 to about 36 carbon atoms. However, alcohols containing from about 4 to about 24 carbon atoms are preferred and alcohols containing from about 10 to about 18 carbon atoms are those most preferred as being most common in commercial processes.

The process of the instant invention can be carried out at ambient pressures. However, pressures of up to 100 pounds per square inch gauge (psig) can also be used. Pressures below about 60 psig are preferred. In addition, pressures below ambient can be used. It is clear that while pressure or lack of pressure is not a detriment to the process of the instant invention, it is simply more convenient to carry out the reaction in the pressure range of from about atmospheric to about 100 psig.

The alkoxylations of the instant invention are normally carried out with materials or mixtures of materials such as ethylene oxide or propylene oxide. However, the process of the instant invention will be effective for any adducting material desired. Of those possible, both ethylene oxide and propylene oxide are preferred, and of these, ethylene oxide is most preferred.

Reaction products can have any desired content of adducting material. For example, ethylene oxide will normally comprise from about 30 to about 80% content based on weight. However, for most purposes, the content of ethylene oxide will range from about 40% to about 70% by weight. The weight of adducting material present in the reaction is not critical other than the minimum amount necessary to provide sufficient units to reach the mole adduct level desired for the alcohols being reacted.

The strontium catalysts of the instant invention are basic catalysts which provide a sharp distribution as to the mole adducts formed while reducing greatly the amount of unreacted free alcohols and undesirable by-products normally formed in alkylene oxide adducts. That strontium is effective in surprising, since of the prior art basic catalysts known, barium oxide when used alone will yield sharp distribution with lowered amounts of by-products, but metal oxides of calcium and magnesium when used alone show no significant ethoxylation activity. It has now been discovered according to the present invention that strontium hydride or strontium metal alone will catalyze these reactions without an unduly long induction period. In addition, it has been found that strontium bases such as strontium oxide, strontium hydroxide and hydrated strontium hydroxides likewise catalyze alkoxylation reactions. However, for these materials a more lengthy induction period in the order of about 220 minutes occurs before significant ethoxylation activity is noted.

For purposes of the instant invention, the strontium catalyst can be strontium metal alone, strontium hydride, strontium oxide alone, strontium hydroxide, and strontium hydroxide hydrates. Any of these strontium compounds are effective in the process of the instant invention without the necessity of using a co-catalyst. However, as set forth in our copending U.S. Pat. No. 4,223,164, the induction period for the strontium oxide, hydroxide and hydrated strontium hydroxide can be reduced by using phenol or substituted phenol co-catalysts in an effective amount. It was previously thought that these strontium bases were not effective when used alone. However, it has since been discovered that these catalysts are effective when used alone, but merely require a longer induction period. When used, these catalyst mixtures can be used in any desired quantity or any mixture. The larger the quantity used, the more quickly the reaction goes to completion, although larger quantities do not appear to significantly alter the distribution obtained.

Representative examples of strontium containing catalysts are strontium metal, strontium hydride, strontium oxide, $Sr(OH)_2$ and $Sr(OH)_2 \cdot XH_2O$, wherein X represents the number of water molecules present. X is not a critical number, but monohydrate and octahydrate are common commercial forms.

For practical purposes, normally from about 0.05 to about 5.0 weight percent strontium catalyst based upon the weight of the alcohol to be reacted would be present in the reaction. These catalysts are effective in the absence of promoters or co-catalysts previously believed necessary but with the exception of strontium metal or strontium hydride require a significant induction period before reaction begins. From about 0.1% to about 2% by weight is preferred when strontium hydride or strontium metal is used, lower levels by weight can be used. Preferred levels for these catalysts are from about 0.1 to about 1.0 by weight.

While the instant invention is effective with all classes of alcohol, alkanols are preferred. Of the alkanols, primary, secondary, linear and branched, linear and branched primary alkanols are the most commonly used and are the preferred alcohols of the instant invention. Representative examples of such alcohols are those derived by hydrogenation of natural fats and oils, such as CO and TA alcohols, trademark of and sold by Proctor and Gamble Co., such as CO-1214N alcohol, CO-1618 alcohol, and TA 1618 alcohol, and ADOL alcohols, trademark of and sold by Ashland Oil Co., such as ADOL 54 alcohol, ADOL 61 alcohol, ADOL 64 alcohol, ADOL 60 alcohol and ADOL 66 alcohol. Alcohols produced by Ziegler chemistry can also be ethoxylated. Examples of these alcohols are ALFOL alcohols, trademark of and sold by Conoco Inc., such as ALFOL 1012 alcohol, ALFOL 1214 alcohol, ALFOL 1412 alcohol, ALFOL 1618 alcohol, ALFOL 1620 alcohol; and EPAL alcohols, trademark of and sold by Ethyl Chemical Co., such as EPAL 1012 alcohol, EPAL 1214 alcohol, EPAL 1418 alcohol. The invention is extremely useful for oxo alcohols (hydroformylation) produced from olefins. Examples of such alcohols are NEODOL alcohol, trademark of and sold by Shell Oil Co., such as NEODOL 23 alcohol, NEODOL 25 alcohol, NEODOL 45 alcohol; TERGITOL-L, trademark of Union Carbide Corp., such as TERGITOL-L 125 alcohol; LIAL alcohols, trademark of and sold by Liquichimica Co. such as LIAL 125; and isodecyl and tridecyl alcohols, sold by Exxon Corp., such as isodecyl alcohol and tridecyl alcohol. Guerbet alcohols can also be ethoxylated. Representative examples of these alcohols are STANDAMUL alcohol, trademark of and sold by Henkel Chemical Co., such as STANDAMUL GT-12 alcohol, STANDAMUL GT-16 alcohol, STANDAMUL GT-20 alcohol, STANDAMUL GT-1620 alcohol. Secondary alcohols can also be used, such as TERGITOL 15 alcohol, trademark of and sold by Union Carbide Corp. Representative examples of such alcohols are 1-decanol; 1-undecanol; 1-dodecanol; 1-tridecanol; 1-tetradecanol; 1-pentadecanol; 1-hexadecanol; 1-heptadecanol; 1-octadecanol; 1-nonadecanol; 1-eicosanol; 1-docosanol; 2-methyl-1-undecanol; 2-propyl-1-nonanol; 2-butyl-1-octanol; 2-methyl-1-tridecanol; 2-ethyl-1-dodecanol; 2-propyl-1-undecanol; 2-butyl-1-decanol; 2-pentyl-1-nonanol; 2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetra-decanol; 3-tetradecanol; 4-tetradecanol; 5-tetradecanol; 6-tetradecanol; 7-tetradecanol; 2-hexadecanol; 3-hexadecanol; 4-hexadecanol; 5-hexadecanol; 6-hexadecanol; 7-hexadecanol; 8-hexadecanol; 2-octadecanol; 3-octadecanol; 4-octadecanol; 5-octadecanol; 6-octadecanol; 7-octadecanol; 8-octadecanol; 9-octadecanol; 9-octadecenol-1; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3-butyl-1-undecanol; 3-hexyl-1-undecanol; 3-hexyl-1-tridecanol; 3-octyl-1-tridecanol; 2-methyl-2-undecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-nonanol; 2-methyl-3-undecanol; 2-methyl-4-undecanol; 4-methyl-2-undecanol; 5-methyl-2-undecanol; 4-ethyl-2-decanol; 4-ethyl-3-decanol; tetracosanol; hexacosanol; octacosanol; triacontanoe; dotriacontanol; hexatriacontanol; 2-decyltetradecanol; 2-dodecylhexadecanol; 2-tetradecyloctadecanol; 2-hexadecyleicosanol.

While any alkylene oxide can be used, normally ethylene oxide or propylene oxide are those most commonly used, and of these ethylene oxide is by far the most commonly used commercial adduct to alcohol. Generally, the treatment of alcohol with ethylene oxide yields a non-ionic detergent, since hydrogen bonding to numerous oxygen molecules makes the poly ether end of the molecule water soluble. Alternatively, the ethoxylates can be converted into sulfates and used in the form of alkali metal salts.

The instant invention thus provides for the production of highly efficient alcohol alkoxylates and especially ethoxylates, from primary and secondary branched chained and straight chained alcohols, particularly alkanols. The alcohols normally contain from about 2 to about 36 carbon atoms. The reaction products are useful as non-ionic surface active agents with high wetting powers and are composed of mixtures of monoalkyl ethers of polyethylene glycol.

Thus, in a preferred form of the present invention, ethylene oxide is reacted with a branched chain or straight chain alkanol in the presence of strontium metal, strontium hydride, strontium oxide, strontium hydroxide, hydrated strontium oxides or other strontium bases. No co-catalyst is necessary.

The invention is more concretely described with reference to the examples below wherein all parts and percentages are by weight unless otherwise specified. The examples are provided to illustrate the instant invention and not to limit it.

EXAMPLE 1

A 600 cubic centimeter (cc) stainless steel reactor was charged with 120 grams of Alfol 1214 alcohol (Trademark of and sold by Conoco Inc) and a catalyst. The catalyst was strontium hydride (0.5 grams). After purging the reactor with nitrogen at the rate of 500 cc's per minute for 30 minutes at 150° C., the reactor was evacuated and the temperature was raised to 175° C. Ethylene oxide (EO) was introduced to a total pressure of 40 pounds per square inch gauge (psig) and EO uptake at this constant pressure was measured as a function of time. After ethoxylation, the base was neutralized.

The results of the experiment showed that the strontium hydride was an extremely active catalyst. The results of this experiment are set forth in Table 1.

TABLE 1

| Time/Min. | EO Reacted/grams |
|---|---|
| 0.0 | 0.0 |
| 15.0 | 15.8 |
| 30.0 | 30.2 |
| 45.0 | 64.4 |
| 60.0 | 98.5 |
| 75.0 | 118.2 |
| 90.0 | 115.1 |
| 103.0 | 180.0 |

The reaction rate of the strontium hydride catalyzed ethoxylation is set forth graphically in FIG. 1. The ethoxylate produced a free alcohol level of 1.45 weight percent.

EXAMPLE 2

As a comparative example, a procedure was carried out as described in Example 1 using 0.1 gram sodium hydroxide. No co-catalyst was used. A successful ethoxylation was carried out. The ethoxylate obtained had an alcohol level of 3.6 weight percent.

EXAMPLE 3

An experiment was carried out as described in Example 1 except that 0.8 grams of SrO and 150 grams of NEODOL 25 alcohol (trademark of and sold by Shell Chemical Co., products of a hydroformylation reaction) were used. At a temperature of 178° C., the ethylene oxide uptake was only 16 grams after one hour. The rate increased after approximately 2 hours at reaction temperature. The reaction to produce a 50% EO adduct was completed in 5.4 hours.

EXAMPLE 4

An experiment was carried out exactly as described in Example 1 except that 0.8 grams strontium hydroxide octahydrate was used as the only catalyst. The reaction temperature was 180° C. The reaction mixture was maintained at this temperature for a period of nearly 4½ hours. No appreciable reaction had occurred for the time preceding three hours. After about 190 minutes at 180° C., it was noted that significant ethoxylation activity had begun to occur. Once significant ethoxylation activity had begun, the reaction swiftly went to completion. A sample of the ethoxylate was obtained and it was determined by gas chromatography that a free alcohol content of 6.1% was obtained. A comparison of the reactions of strontium hydride and strontium hydroxide octahydrate is set forth in FIG. 1.

EXAMPLE 5

A stainless steel reactor was charged with 184 grams ALFOL 1412 alcohol and 0.5 grams strontium metal. Temperature was raised to 178° C. with a continuous nitrogen purge of 500 cc minute. After brief evacuation, ethylene oxide was charged to 40 psig. The ethoxylation proceeded as set forth in Table 2.

TABLE 2

| Time/min. | EO reacted/g |
|---|---|
| 15 | 11 |
| 30 | 13 |
| 45 | 18 |
| 60 | 28 |
| 75 | 45 |
| 90 | 73 |
| 105 | 107 |

TABLE 2-continued

| Time/min. | EO reacted/g |
| --- | --- |
| 110 | 120 |

EXAMPLE 6

A stainless steel reactor (600 cc) is charged with 180 grams ALFOL 12 alcohol and 0.8 g $Sr(OH)_2 \cdot 8H_2O$. After purging with $N_2$ at 250 cc/minute for one hour at 150° C. the reactor is evacuated and the temperature raised to about 178° C. Propylene oxide (PO) is introduced to a total pressure of about 40 psig, and PO uptake of 120 grams allowed to proceed at this pressure. PO addition requires more time to complete than a comparable preparation to a similar level using ethylene oxide (EO). After propoxylation, the catalyst is neutralized. The resulting product has narrow, peaked adduct distribution and low free alcohol content when compared to similar preparations using alkali metal catalysts.

In addition, the catalysts and methods of the instant invention are well suited for the ethoxylation of alcohols produced by hydroformylation (or oxo/hydrogenation) by Guerbet reactions, and for alcohol produced by aluminum chemistry. Many of the alcohols have, in the past, presented difficulty when used as reactants for alkoxylation because of the high concentration of unreacted alcohols. However, catalysts of the instant invention produce extremely good ethoxylate using these alcohols. Those produced using strontium metal and/or strontium hydride are especially effective. The superiority of the strontium base catalyst of the instant invention are evident when viewing actual samples obtained. For example, at low ethoxylation concentrations such as 30 to 40%, the strontium catalysts produce water clear ethoxylated material while alkali metal catalyzed ethoxylates are hazy or cloudy using a 12 to 15 carbon atom alkanol. The difference is even more apparent at high concentration levels such as 65% ethoxylation. At these concentration levels, alkali metal catalyzed ethoxylates are an off-white solid while strontium-produced ethoxylates are a water-clear fluid.

It is readily apparent that by practicing the instant invention, high mole adduct ethoxylates of alcohols can be obtained in a very narrow highly desirable distribution range while producing very low amounts of by-products and unreacted free alcohols. In addition, strontium hydride and strontium metal produce desirably fast reaction rates and greatly reduced induction periods with additional benefits. As set forth in U.S. Pat. No. 4,223,164, gas liquid chromatographic (glc) analysis of these ethoxylation experiments show that ethoxylates made with basic strontium-containing catalysts are low in by-products and unreacted free alcohols. A comparison with sodium hydroxide catalyzed reactions show these new catalyst systems preferable to known basic catalyst systems.

Although exemplified as batch reactions, the catalysts in the instant invention are extremely well suited to continuous reaction methods. This is true since the reaction products are of extremely high quality and quantity.

While certain embodiments and details have been shown for the purpose of illustrating this invention, it will be apparent to those skilled in this art that various changes and modifications may be made herein without departing from the spirit or scope of the invention.

We claim:

1. A method for the alkoxylation of alkanols comprising contacting said alkanols with a suitable alkoxylating material in the presence of a strontium-containing catalyst system comprising at least one material selected from the group consisting of strontium metal, strontium hydride, strontium oxide, strontium hydroxide, and hydrated strontium hydroxide, wherein said contacting is carried out for a sufficient time for reaction to occur to the extent desired, said reaction carried out at temperatures of from about 90° C. to about 260° C.

2. A method as described in claim 1 wherein the alkoxylation is carried out using ethylene oxide or propylene oxide.

3. A method as described in claim 2 wherein the catalyst is selected from the group consisting of strontium metal, strontium hydride, or mixtures of these.

4. A method as described in claim 3 wherein the reaction is carried out at pressures up to about 100 psig.

5. A method as described in claim 4 wherein the ethylene oxide/propylene oxide adduct mole ratios are from about 30 weight percent to about 80 weight percent of the reaction product.

6. A method as described in claim 5 wherein the strontium catalyst is present in amounts of from about 0.15 to about 5% by weight based on the alkanol to be reacted.

7. A method as described in claim 6 wherein the alkanol is the product of a hydroformylation/hydrogenation reaction.

8. A method as described in claim 6 wherein the alkanol is a primary alkanol containing from about 4 to about 36 carbon atoms.

9. A method as described in claim 1 when carried out in a continuous fashion.

10. A method as described in claim 2 wherein the catalyst is selected from the group consisting of strontium oxide, strontium hydroxide, and hydrated strontium hydroxide, and the reaction temperature is from about 170° C. to about 200° C.

11. A method as described in claim 10 wherein the reaction is carried out at pressures up to about 100 psig.

12. A method as described in claim 11 wherein the ethylene oxide/propylene oxide adduct mole ratios are from about 30 weight percent to about 80 weight percent of the reaction product.

13. A method as described in claim 12 wherein the strontium catalyst is present in amounts of from about 0.15 to about 5% by weight based on the alkanol to be reacted.

14. A method as described in claim 13 wherein the alkanol is a primary alcohol containing from 4 to 36 carbon atoms.

15. A method as described in claim 13 wherein the alkanol is a product of the hydroformylation/hydrogenation reaction.

* * * * *